(12) United States Patent
Nortman et al.

(10) Patent No.: US 12,318,543 B2
(45) Date of Patent: Jun. 3, 2025

(54) ROBOTIC VENTILATION METHOD CONFIGURED FOR AUTOMATIC GAS DELIVERY

(71) Applicant: Restful Robotics, Inc., Sunrise, FL (US)

(72) Inventors: Scott Nortman, Sunrise, FL (US); David Jassir, Davie, FL (US)

(73) Assignee: Restful Robotics Inc., Sunrise, FL (US)

( * ) Notice: Subject to any disclaimer, the term of this patent is extended or adjusted under 35 U.S.C. 154(b) by 828 days.

(21) Appl. No.: 17/521,700

(22) Filed: Nov. 8, 2021

(65) Prior Publication Data

US 2022/0080143 A1 Mar. 17, 2022

Related U.S. Application Data

(63) Continuation-in-part of application No. PCT/US2020/059803, filed on Nov. 10, 2020.

(60) Provisional application No. 62/933,620, filed on Nov. 11, 2019.

(51) Int. Cl.
*A61M 16/00* (2006.01)
*A61M 16/06* (2006.01)
*A61M 16/08* (2006.01)

(52) U.S. Cl.
CPC .......... *A61M 16/06* (2013.01); *A61M 16/022* (2017.08); *A61M 16/0616* (2014.02); *A61M 16/0683* (2013.01); *A61M 16/0875* (2013.01); *A61M 2205/0216* (2013.01); *A61M 2205/13* (2013.01); *A61M 2210/0618* (2013.01); *A61M 2210/0625* (2013.01); *A61M 2230/04* (2013.01); *A61M 2230/18* (2013.01); *A61M 2230/42* (2013.01); *A61M 2230/50* (2013.01); *A61M 2230/63* (2013.01)

(58) Field of Classification Search
CPC ................ A61M 16/06; A61M 16/022; A61M 16/0683; A61B 34/30; A61B 90/50
See application file for complete search history.

(56) References Cited

U.S. PATENT DOCUMENTS

2008/0092894 A1* 4/2008 Nicolazzi ............. A61B 5/6814
128/204.23
2012/0211008 A1* 8/2012 Perine ................. A61M 16/085
128/204.23

FOREIGN PATENT DOCUMENTS

CN 108969858 A * 12/2018 ........ A61M 16/0051

* cited by examiner

*Primary Examiner* — Margaret M Luarca
(74) *Attorney, Agent, or Firm* — J. Steven Svoboda (57) ABSTRACT

A method includes: obtaining a desired value for a parameter relevant to the automatic delivery of breathable gas; saving, by the system, the desired parameter value; finding, by the system, an actual value of the parameter; querying, by the system, whether the actual parameter value agrees with the desired parameter value; determining, by the system, that the actual parameter value does not agree with the desired parameter value; adjusting, by the system, a system setting so as to attain the desired parameter value; querying, by the system, whether the actual revised parameter value agrees with the desired parameter value; and repeating, by the system, the steps of determining, adjusting, and querying whether the actual revised parameter value agrees with the desired parameter value until the actual revised parameter value agrees with the desired parameter value.

4 Claims, 8 Drawing Sheets

OBTAINING A DESIRED VALUE OF A PARAMETER BY A SYSTEM COMPRISING: A ROBOT COMPRISING AN ARM, THE ARM COMPRISING A FLANGE, THE FLANGE COUPLED TO AN END OF THE ARM, THE ARM CONFIGURED TO MOVE THE FLANGE ALONG A DEGREE OF FREEDOM, THE ARM FURTHER COMPRISING A KINEMATIC MOUNT; A MASK COUPLED TO THE FLANGE BY A MOUNTING FEATURE CONFIGURED FOR INTERMITTENT ATTACHMENT, THE MASK CONFIGURED TO DELIVER THE GAS TO A USER, WHEREIN THE KINEMATIC MOUNT IS USABLE TO DO ONE OR MORE OF ORIENT AND LOCATE THE MASK WITH RESPECT TO THE FLANGE; A MASK COUPLED TO THE ROBOT, WHEREIN THE MASK IS COUPLED TO THE FLANGE BY A MOUNTING FEATURE CONFIGURED FOR INTERMITTENT ATTACHMENT, THE MOUNTING FEATURE COMPRISING THE KINEMATIC MOUNT, THE MOUNTING FEATURE FURTHER COMPRISING AN OPENING, WHEREIN THE MOUNTING FEATURE FURTHER COMPRISES A SENSOR, THE SENSOR CONFIGURED TO VERIFY THAT PROPER SEATING HAS OCCURRED OF THE MASK ON THE USER, WHEREIN A SPATIAL ALIGNMENT OF THE MASK WITH RESPECT TO THE KINEMATIC MOUNT IS KNOWN A PRIORI, WHEREIN THE MASK FURTHER COMPRISES A FIDUCIAL MARKER, THE FIDUCIAL MARKER CONFIGURED TO BE TRACKED BY A TRACKING SYSTEM; A VENTILATOR COUPLED TO THE MASK, THE VENTILATOR CONFIGURED TO DELIVER THE GAS TO THE MASK, WHEREIN THE GAS PASSES THROUGH THE OPENING, WHEREIN THE OPENING COMPRISES A SENSOR, THE SENSOR CONFIGURED TO DETECT THE GAS; A GAS TUBE COUPLED TO BOTH THE MASK AND THE VENTILATOR, THE GAS TUBE CONFIGURED TO CARRY THE GAS BETWEEN THE VENTILATOR AND THE MASK; A CONTROLLER CONFIGURED TO CHANGE A POSE OF THE MASK, THE CONTROLLER FURTHER CONFIGURED TO DELIVER GAS FROM THE VENTILATOR TO THE MASK, WHEREIN FOLLOWING A START OF DELIVERY OF PRESSURIZED GAS TO THE USER, THE CONTROLLER COMMANDS THE ARM TO MAINTAIN BOTH AN APPROPRIATE CONTACT FORCE WITH RESPECT TO THE USER'S FACE AND AN APPROPRIATE POSITION WITH RESPECT TO THE USER'S FACE, WHEREIN THE APPROPRIATE CONTACT FORCE AND THE APPROPRIATE POSITION CREATE A SAFE AND EFFECTIVE CONTACT ENGAGEMENT BETWEEN THE MASK AND THE FACE OF THE USER, WHEREIN FOLLOWING A FAILURE OF THE SYSTEM TO MAINTAIN THE ARM AT BOTH AN APPROPRIATE CONTACT FORCE AND AN APPROPRIATE POSITION, THE SYSTEM IS CONFIGURED TO RETRACT THE ARM SO AS TO MOVE THE MASK AWAY FROM THE FACE OF THE USER, WHEREIN THE SYSTEM IS FURTHER CONFIGURED, FOLLOWING RETRACTION OF THE ARM, TO GO INTO A MODE IN WHICH THE SYSTEM AWAITS ENTRY BY THE USER INTO A REQUISITE SLEEP STATE, WHEREIN UPON ENTRY BY THE USER INTO THE REQUISITE SLEEP STATE, THE SYSTEM MOVES THE ARM TOWARD THE FACE OF THE USER; A TRACKING SYSTEM, THE TRACKING SYSTEM CONFIGURED TO CAPTURE IMAGE DATA OF ONE OR MORE OF THE MASK AND A FACE OF THE USER, THE TRACKING SYSTEM CONFIGURED TO IDENTIFY A FACE FEATURE POINT, WHEREIN THE FACE FEATURE POINT COMPRISES ONE OR MORE OF AN EYE CENTER POINT, A NOSE CENTER POINT, A MOUTH LATERAL POINT, AND A MOUTH CENTER POINT, WHEREIN THE SYSTEM MOVES THE ARM TOWARD THE FACE OF THE USER AFTER THE FACE FEATURE POINT IS IDENTIFIED, WHEREIN THE CONTROLLER IS CONFIGURED TO CHANGE THE MASK POSE BASED ON ONE OR MORE OF THE IMAGE DATA, LAPSE OF A PREDETERMINED PERIOD OF TIME, AND AN ESTIMATED SLEEP STATE OF THE USER, WHEREIN THE PREDETERMINED PERIOD OF TIME REPRESENTS AN INDICATION BY THE USER TO THE SYSTEM THAT THE USER IS GOING TO SLEEP AFTER THE PREDETERMINED PERIOD OF TIME, WHEREIN THE ESTIMATED SLEEP STATE COMPRISES ONE OR MORE OF A REQUISITE SLEEP STATE AND AN ESTIMATION OF STABILITY OF THE USER'S SLEEP STATE, WHEREIN THE SYSTEM PLACES THE MASK ON THE FACE OF THE USER AFTER THE PREDETERMINED PERIOD OF TIME HAS LAPSED, THE ROBOT COMPRISING

FIG. 6 CONTINUED

ROBOTIC VENTILATION METHOD CONFIGURED FOR AUTOMATIC GAS DELIVERY

PRIORITY CLAIM

The present application is a continuation-in-part that claims the priority benefit of Patent Cooperation Treaty application number PCT/US2020/059803, filed Nov. 10, 2020 and entitled, "Automatic Placement of a Mask," which in turn claims priority from U.S. provisional patent application No. 62/933,620 filed Nov. 11, 2019 and entitled "Apparatus and Method for Automatic Placement of a CPAP Mask."

CROSS-REFERENCE TO RELATED APPLICATION

This application contains subject matter that is related to the subject matter of the following applications, which are assigned to the same assignee as this application. The below-listed application is hereby incorporated herein by reference in its entirety:

"ROBOTIC VENTILATION SYSTEM FOR CORRECT MASK PLACEMENT," by Nortman, et al., co-filed herewith.

FIELD OF THE INVENTION

The present disclosure relates to medical systems, devices, and methods, and more specifically to a robotic ventilation method, and still more specifically to a robotic ventilation method configured for automatic gas delivery.

The figures depict various embodiments for purposes of illustration only. One skilled in the art will readily recognize from the following discussion that alternative embodiments of the structure and methods illustrated herein may be employed without departing from the principles described herein.

SUMMARY

A robotic ventilation method for automatic delivery of breathable gas includes: obtaining a desired value for a parameter relevant to the automatic delivery of the breathable gas using a system comprising: a robot comprising an arm, the arm comprising a flange, the flange coupled to an end of the arm, the arm configured to move the flange along a degree of freedom; a mask coupled to the flange, the mask configured to deliver gas to a user; a ventilator coupled to the mask, the ventilator configured to deliver the gas to the mask; a gas tube coupled to both the mask and the ventilator, the gas tube configured to carry gas between the ventilator and the mask; a controller configured to change a pose of the mask, the controller further configured to control the delivery of the gas from the ventilator to the user; a tracking system, the tracking system configured to capture image data of one or more of the mask and a face of the user, wherein the controller is configured to change the mask pose based at least in part on the image data; and a sensor, the sensor configured to sense one or more of a parameter value; saving, by the system, the desired parameter value; finding, by the system, an actual value of the parameter; querying, by the system, whether the actual parameter value agrees with the desired parameter value; determining, by the system, that the actual parameter value does not agree with the desired parameter value; adjusting, by the system, a system setting so as to attain the desired parameter value; querying, by the system, whether the actual revised parameter value agrees with the desired parameter value; and repeating, by the system, the steps of determining, adjusting, and querying whether the actual revised parameter value agrees with the desired parameter value until the actual revised parameter value agrees with the desired parameter value.

A robotic ventilation method for automatic delivery of breathable gas, includes: obtaining a desired value for a parameter affected by the automatic delivery of the breathable gas using a system comprising: a robot comprising an arm, the arm comprising a flange, the flange coupled to an end of the arm, the arm configured to move the flange along a degree of freedom; a mask coupled to the flange, the mask configured to deliver gas to a user; a ventilator coupled to the mask, the ventilator configured to deliver the gas to the mask; a gas tube coupled to both the mask and the ventilator, the gas tube configured to carry gas between the ventilator and the mask; a controller configured to change a pose of the mask, the controller further configured to control the delivery of the gas from the ventilator to the user; and a tracking system, the tracking system configured to capture image data of one or more of the mask and a face of the user, wherein the controller is configured to change the mask pose based at least in part on the image data; and a sensor, the sensor configured to sense a parameter value; saving, by the system, the desired parameter value; using the system, finding an actual value of the parameter; querying whether the actual parameter value agrees with the desired parameter value; and determining that the actual parameter value agrees with the desired parameter value.

A robotic ventilation method for automatic delivery of breathable gas includes: obtaining a desired value of a parameter affected by the automatic delivery of the breathable gas using a system comprising: a robot comprising an arm, the arm comprising a flange, the flange coupled to an end of the arm, the arm configured to move the flange along a degree of freedom; a mask coupled to the flange, the mask configured to deliver gas to a user; a ventilator coupled to the mask, the ventilator configured to deliver the gas to the mask, wherein following a start of delivery of pressurized gas to the user, the system commands the robotic arm to maintain both an appropriate contact force with respect to a face of the user face and an appropriate position with respect to the user's face, wherein following movement of the face of the user, the robotic arm is configured to do one or more of move its location and change the contact force to maintain both an appropriate contact force with respect to a face of the user face and an appropriate position with respect to the user's face, wherein following a failure of the system to maintain both an appropriate contact force and an appropriate position, the system is configured to retract the robotic arm so as to move the mask away from the face of the user, wherein following retraction of the robotic arm, if the user is in a requisite sleep state, the system is configured to move the robotic arm toward the face of the user, wherein following retraction of the robotic arm, if the user is awake, the system is configured to go into a mode in which it awaits entry into a requisite sleep state by the user, wherein following the entry into the requisite sleep state by the user, the system moves the robotic arm toward the face of the user; a gas tube coupled to both the mask and the ventilator, the gas tube configured to carry gas between the ventilator and the mask; a controller configured to change a pose of the mask, the controller further configured to control the delivery of the gas from the ventilator to the user, wherein the controller is further configured to change the mask pose based on one or more of the image data and an estimated sleep state of the user, wherein the estimated sleep state comprises one or more of a requisite sleep state and an estimation of stability of the user's sleep state, wherein the system transitions from the sleep state to an approach state if the system determines the estimated sleep state of the user is the requisite sleep state and if the system further determines that the estimated sleep state of the user is stable, wherein the system transitions from the sleep state to a wait for sleep state in which the system waits if the system determines one or more of that the estimated sleep state of the user is not the requisite sleep state and that the estimated sleep state of the user is not stable; a tracking system, the tracking system configured to capture image data of one or more of the mask and the face of the user, the tracking system comprising an illumination system configured to emit light in a field of view of the tracking system; a biometric sensor system, the biometric sensor system comprising a biometric sensor, wherein the controller is configured to change the mask pose based at least in part on biometric data from the biometric sensor system; and an image processing block configured to process the image data, the image processing block further configured to identify a face feature point, wherein the face feature point comprises one or more of an eye center point, a nose center point, a mouth lateral point, and a mouth center point, wherein the system moves the robotic arm toward the face of the user after the face feature point is identified; saving, by the system, the desired parameter value; using the system, finding an actual value of the parameter; querying whether the actual parameter value agrees with the desired parameter value; determining that the actual parameter value does not agree with the desired parameter value; adjusting a system setting so as to attain the desired parameter value; querying whether the actual revised parameter value agrees with the desired parameter value; and repeating the steps of determining, adjusting, and querying whether the actual revised parameter value agrees with the desired parameter value until the actual revised parameter value agrees with the desired parameter value.

A robotic ventilation method for automatic delivery of breathable gas includes: obtaining a desired value of a parameter affected by the automatic delivery of the breathable gas using a system comprising: a robot comprising an arm, the arm comprising a flange, the flange coupled to an end of the arm, the arm configured to move the flange along a degree of freedom; a mask coupled to the flange, the mask configured to deliver gas to a user; a ventilator coupled to the mask, the ventilator configured to deliver the gas to the mask, wherein following a start of delivery of pressurized gas to the user, the system commands the robotic arm to maintain both an appropriate contact force with respect to a face of the user face and an appropriate position with respect to the user's face, wherein following movement of the face of the user, the robotic arm is configured to do one or more of move its location and change the contact force to maintain both an appropriate contact force with respect to a face of the user face and an appropriate position with respect to the user's face, wherein following a failure of the system to maintain both an appropriate contact force and an appropriate position, the system is configured to retract the robotic arm so as to move the mask away from the face of the user, wherein following retraction of the robotic arm, if the user is in a requisite sleep state, the system is configured to move the robotic arm toward the face of the user, wherein following retraction of the robotic arm, if the user is awake, the system is configured to go into a mode in which it awaits entry into a requisite sleep state by the user, wherein following the entry into the requisite sleep state by the user, the system moves the robotic arm toward the face of the user; a gas tube coupled to both the mask and the ventilator, the gas tube configured to carry gas between the ventilator and the mask; a controller configured to change a pose of the mask, the controller further configured to control the delivery of the gas from the ventilator to the user, wherein the controller is further configured to change the mask based on one or more of the image data and an estimated sleep state of the user, wherein the estimated sleep state comprises one or more of a requisite sleep state and an estimation of stability of the user's sleep state, wherein the system transitions from the sleep state to an approach state if the system determines the estimated sleep state of the user is the requisite sleep state and if the system further determines that the estimated sleep state of the user is stable, wherein the system transitions from the sleep state to a wait for sleep state in which the system waits if the system determines one or more of that the estimated sleep state of the user is not the requisite sleep state and that the estimated sleep state of the user is not stable; a tracking system, the tracking system configured to capture image data of one or more of the mask and the face of the user, the tracking system comprising an illumination system configured to emit light in a field of view of the tracking system; a biometric sensor system, the biometric sensor system comprising a biometric sensor, wherein the controller is configured to change the mask pose based at least in part on biometric data from the biometric sensor system; and an image processing block configured to process the image data, the image processing block further configured to identify a face feature point, wherein the face feature point comprises one or more of an eye center point, a nose center point, a mouth lateral point, and a mouth center point, wherein the system moves the robotic arm toward the face of the user after the face feature point is identified; saving, by the system, the desired parameter value; using the system, finding an actual value of the parameter; querying whether the actual parameter value agrees with the desired parameter value; and determining that the actual parameter value agrees with the desired parameter value.

DETAILED DESCRIPTION

The disclosure describes a system and method for correct placement and for proper force application of a ventilator mask onto a face of a user, and for maintaining the proper placement and force application of the mask while the user does one or more of sleep and move.

A robotic arm has the mask operatively coupled to its distal end, and a robot base is placed beside the user. The reach and dexterity of the robotic arm can allow for correct placement and for proper force application of the mask onto the face of the user while the user does one or more of lie in bed and move during sleep.

The distal end of the robotic arm can also be operatively coupled to a computer vision system that views the face of the user and optically tracks needed facial features, in real-time, to cause the robotic arm to maintain correct alignment of the mask with the face of the user.

A biometric sensor system can measure and analyze signals of the user to determine a sleep state of the user in real-time, and can cause the robotic arm to position and orient the mask after the user has entered a specified sleep state.

Figure 1A:
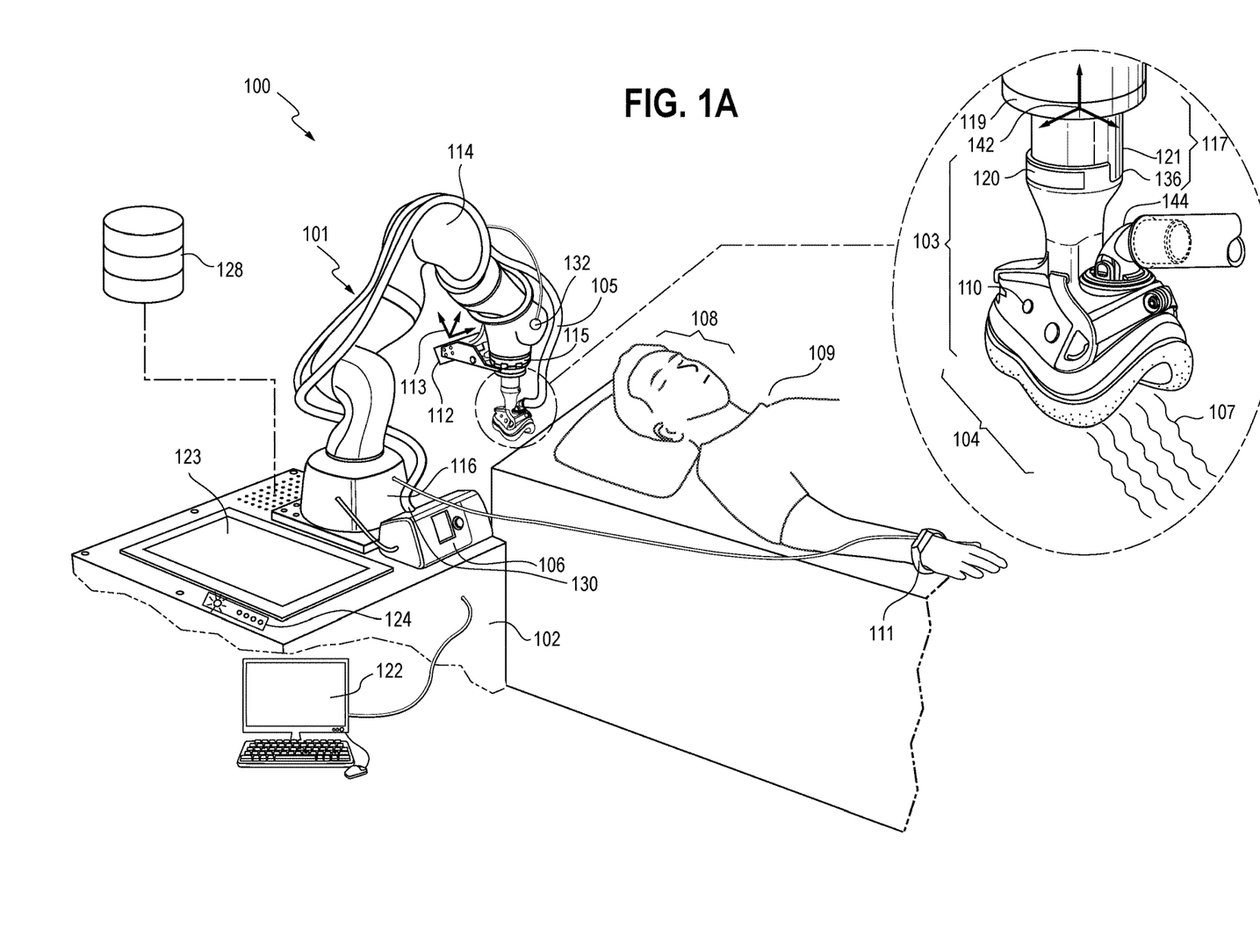
FIG. 1A is a drawing of a robotic ventilation system.

FIG. 1A is a drawing of a robotic ventilation system 100. The system 100 comprises a robot 101 and a base 102 operably connected to the robot 101. The robot 101 comprises a mask system 103. The mask system 103 comprises a mask 104, the mask 104 configured to deliver the breathable gas 107 to the user 109. The mask 104 comprises one or more of a face mask, a partial face mask, a nasal mask, a mouth mask, a nasal pillow mask, and a nasal plug mask. The robot 101 further comprises a tube 105, the tube 105 operably connected to the mask system 103. The base 102 comprises a ventilator 106, the ventilator 106 configured to deliver breathable gas 107 to the mask 104 through the tube 105. The mask 104 then delivers the gas 107 to a face 108 of a user 109. Alternative embodiments comprise the ventilator 106 as a standalone ventilator 106. Alternatively, or additionally, the ventilator 106 is positioned outside of the base 102.

The system 100 is configured to deliver the breathable gas 107 to the user 109 via the mask 104. For example, the system 100 delivers the breathable gas 107 to the user 109 via the mask 104 after detecting a state of the user 109. More specifically, the system 100 delivers the breathable gas 107 to the user 109 via the mask 104 after detecting a requisite sleep state of the user 109. The requisite sleep state may be predetermined by the user 109. Alternatively, or additionally, the requisite sleep state may be determined by the system 100. For example, the requisite sleep state may be calculated by the system 100. For example, the requisite sleep state comprises one or more of a wakeful state, a stage 1 non-rapid eye movement (non-REM) sleep state, a stage 2 non-REM sleep state, a stage 3 non-REM sleep state, and an REM sleep state. Even more specifically, the system 100 delivers the breathable gas 107 to the user 109 after the user 109 falls asleep. Alternatively, or additionally, the system 100 delivers the breathable gas 107 to the user 109 after fulfillment of a time-based condition. For example, the system 100 delivers the breathable gas 107 to the user 109 after one or more of passage of a predetermined amount of time and after a predetermined time of day is reached.

Optionally, the mask 104 further comprises a fiducial marker 110. The fiducial marker 110 comprises a tracked object 110 placed at a known pose in a sensing area of a tracking system that can be viewed by the tracking system and can serve as a reference for the tracking system.

For example, the fiducial marker comprises a circular fiducial marker such as the MBA08MMA manufactured by NaturalPoint, Inc., of Corvallis, Oregon (www.naturalpoint.com). For example, the fiducial marker comprises a spherical fiducial marker such as the MKR064M3-10 manufactured by NaturalPoint, Inc., of Corvallis, Oregon (www.naturalpoint.com). For example, the fiducial marker comprises a square fiducial marker such as the ArUco developed by Universitario de Rabanales, University of Córdoba, 14071, Córdoba, Spain (www.uco.es).

The robot 102 further comprises a biometric sensor system 111, the biometric sensor system 111 configured to sense biometric information regarding the user 109. For example, the biometric information comprises one or more of a heart rate, a respiratory rate, a temperature, a blood oxygen saturation level, an eye state, motion or lack thereof, an estimated sleep state, a sleep profile, a blood pressure, a pulse rate, a temperature, an eye state, a height, a weight, an age, and other biometric information. For example, tracked facial features of the user can be observed using a non-computer-vision-based approach, such as radar, LIDAR, ultrasound, or any other suitable spatial measuring method. For example, the current sleep state is determined using a remote camera comprised in the biometric sensor system 111. For example, the biometric sensor system 111 comprises one or more of a camera and a watch.

For example, the biometric sensor system 111 is physically attached to the user 109. Alternatively, or additionally, the biometric sensor system 111 comprises a remote biometric sensor system 111 that is not physically attached to the user 109. For example, the biometric sensor system 111 is comprised in a virtual assistant device such as the Alexa device sold by Amazon.com of Seattle, Washington (www.amazon.com).

The system 100 further comprises a tracking system 112 configured to track one or more of the mask system 103, the fiducial marker 110, and a face feature point of the user 109. The tracking system is further configured to capture image data. The image data comprises a facial feature (not shown in FIG. 1A) of the user 109. For example, the tracking system 112 comprises a camera system configured to capture the image data.

While a computer vision system 112 is a preferred implementation of the invention, more broadly, any tracking system 112 will work, including one or more of a computer vision system, a radio detection and ranging (RADAR) tracking system, a light detection and ranging (LIDAR) tracking system, an ultrasound tracking system, and any other suitable spatial measuring method. The tracking system 112 is configured to identify a face feature point. The face feature point comprises one or more of an eye center point, a nose center point, a mouth lateral point, and a mouth center point.

The robot 102 further comprises an arm 114, the arm configured to do one or more of position the mask 104 with respect to the user 109 and orient the mask 104 with respect to the user 109. The arm 114 comprises a flange 115, the flange 115 coupled to an end of the arm 114. The arm 114 can have one or more degrees of freedom. Alternatively, or additionally, the flange 115 can have one or more degrees of freedom. The arm 114 is configured to move the flange 115 along a degree of freedom. For example, the arm 114 can have seven degrees of freedom. For example, the arm 114 can have fewer degrees of freedom, for example six degrees of freedom, or more degrees of freedom, for example eight degrees of freedom. For example, the six degrees of freedom comprise one or more of three directions describing a location of the arm 114 and three directions describing an orientation of the arm 114. The robot 102 further comprises a robot base 116 configured to support the arm 114. The flange 115 is coupled to an end of the arm 114 that is distal from the robot base 116. The mask 104 is also coupled to the flange 115.

The arm 114 further comprises a kinematic mount 117, the kinematic mount 117 usable to do one or more of orient and locate the mask 104 with respect to the flange 115. Preferably, but not necessarily, the kinematic mount 117 is usable to both orient the mask with respect to the flange 115 and locate the mask 104 with respect to the flange 115. Alternatively, or additionally, the arm 114 comprises a mount other than a kinematic mount, attaching to the flange 115. The kinematic mount 117 comprises a flange kinematic mount 119, the flange kinematic mount 119 mounted to the flange 115. The kinematic mount 117 further comprises a mask system kinematic mount 120, the mask system kinematic mount 120 mounted to the mask system 103. The mask system kinematic mount 120 attaches to the flange kinematic mount 119 by a mounting feature 121. The mounting feature 121 is configured for intermittent attachment of the flange kinematic mount 119 and the mask system kinematic mount 120. For example, de-attachment of the flange kinematic mount 119 and the mask system kinematic mount 120 may be necessary for one or more of cleaning, sterilizing, sanitizing, and replacing, and the like. For example, the mask system kinematic mount 120 comprises an SB1 kinematic mount base manufactured by Thorlabs of Newton, New Jersey (www.thorlabs.com), the mounting feature 121 comprises one or more of a kinematic mounting feature 121, a magnetic mounting feature 121, a mechanical mounting feature 121, and a clamp-on mounting feature 121.

The system 100 is configured to move the arm 114 toward the face 108 of the user 109 after the face feature point is identified. The system 100 is further configured to move the arm 114 so as to bring the mask 104 into contact with the face 108 of the user 109 after the face feature point is identified.

The system 100 is further configured, following bringing the mask 104 into contact with the face 108 of the user 109, to command the arm 114 to maintain one or more of an appropriate contact force with respect to the user's face 108 and an appropriate position with respect to the user's face 108. The appropriate contact force and the appropriate position create a safe and effective contact engagement between the mask 104 and the face 108 of the user 109.

The system 100 is further configured, following bringing the mask 104 into contact with the face 108 of the user 109, to command the arm 114 to maintain both an appropriate contact force with respect to the user's face 108 and an appropriate position with respect to the user's face 108.

The system 100 is further configured, following movement of the face 108 of the user 109, to move the position of the arm 114 so as to maintain an appropriate position with respect to the user's face 108.

The system 100 is further configured, wherein following a failure of the system 100 to maintain the arm 114 at both an appropriate contact force and an appropriate position, to retract the arm 114 so as to move the mask 104 away from the face 108 of the user 109.

The system 100 is further configured, following retraction of the arm 114, to go into a mode in which the system 100 awaits entry by the user 109 into a requisite sleep state. The system 100 is further configured, upon entry by the user 109 into the requisite sleep state, to move the arm 114 toward the face 108 of the user 109.

The tracking system 112 can include one or more of a transmitter configured to transmit a signal describing a biometric signal of the user 109, a transmitter configured to transmit spatial tracking information, a camera system configured to capture image data, a tracking sensor configured to detect the signal, thereby gathering sensor data, and a processor configured to control one or more of aspect of the system 100.

The tracking system 112 comprises a tracking system coordinate frame 113. The tracking system coordinate frame 113 can be defined from a feature of the tracking system 112. For example, the coordinate system of the Intel RealSense Depth Camera D435, sold by Intel Corporation of Santa Clara, California (www.intel.com) locates and orients its camera coordinate system with respect to its left infrared camera. When tracking an object, the tracking system 112 can determine one or more of a coordinate frame and a centroid of the tracked object. When tracking an object feature, the tracking system 112 can determine one or more of a coordinate frame and a centroid of the tracked feature. The coordinate frame can be defined with respect to the tracking coordinate frame 113. Centroid tracking data can be defined with respect to the tracking coordinate frame 113.

The base 102 further comprises a controller 122 configured to control the system 100. For example, the controller 122 comprises one or more of a tracking controller configured to control the tracking system 112, a ventilator controller configured to control the ventilator 106, and another controller. The controller 122 commands the arm 114 to maintain one or more of an appropriate contact force with respect to the user's face 108 and an appropriate position with respect to the user's face 108. The controller 122 commands the arm 114 to maintain both the appropriate contact force with respect to the user's face 108 and the appropriate position with respect to the user's face 108. The controller 122 is further configured to change a pose of the mask 104 based on one or more of the image data, lapse of a predetermined period of time, and an estimated sleep state of the user 109. The estimated sleep state of the user 109 comprises one or more of the requisite sleep state and an estimation of stability of the sleep state of the user 109. The system 100 transitions from the sleep state to an approach state if the system determines that the estimated sleep state of the user 109 is the requisite sleep state and if the system further determines that the estimated sleep state of the user 109 is stable. Alternatively, or additionally, the system 100 transitions from the sleep state to a wait for sleep state in which the system 100 waits if the system 100 determines one or more of that the estimated sleep state of the user 109 is not the requisite sleep state and that the estimated sleep state of the user 109 is not stable.

The controller 122 is further configured to change a pose of the mask 104 based at least in part on biometric data from the biometric sensor system 111.

The base 102 further comprises a display 123 configured to display information to the user 109 regarding the system 100, Optionally, the display 123 includes a user interface 124. The user interface 124 can provide information to the user 109, for example, power status of the system 100. The user interface 124 can include push buttons usable by the user 109 to control the system 100.

For example, the user interface 124 comprises one or more of an indicator, a speaker, a microphone, a button, and a switch. Alternatively, or additionally, the user interface 124 comprises one or more of a standalone interface and an interface comprised in a portion of the system 100 other than the display 123.

The biometric sensor system 111 then transmits the estimated state of the user 109 to the controller 122. The controller 122 can store the estimated state of the user 109 in a database 128.

The biometric sensor system 111 receives biometric data, determines a user parameter based at least in part on the received biometric data, and estimates a state of the user 109 based at least in part on the determined parameter. The biometric sensor system 111 stores in the database 128 one or more of the biometric data, the estimated state of the user, and the determined parameter. The biometric sensor system 111 can send the biometric to the system 100 the one or more of the biometric data, the estimated state of the user, and the determined parameter.

The robot base 116 comprises a set of tube-base connections 130 through which the robot base 116 couples to the gas tube 105. For example, the set of tube-base connections 130 through which the robot base 116 couples to the gas tube 105 can include a system sensor 132 configured to gather sensor data and store gathered data in the database 128. For example, the tube-base connection 130 comprises a tube-base opening 130.

For example, the robot 102 comprises a system sensor 132 configured to sense one or more of forces, torques, currents, voltages, temperatures, and the like. For example, the arm 114 comprises the system sensor 132.

The flange 115 includes a flange-mask connection 136 through which the flange 115 couples to the mask system 103. For example, the flange-mask connection 136 comprises a flange-mask opening 136. The flange-mask connection 136 can include a robot mounting feature 138.

The flange kinematic mount 119 comprises a flange kinematic mount coordinate frame 142 which can be defined from a feature of the flange kinematic mount 119. The robot mounting feature 138 can comprise an opening (not shown). The gas 107 can pass through the opening. A signal can pass through the opening. The opening can comprise a sensor, the sensor configured to detect the gas 107.

The gas tube 105 is coupled to the robot base 116. The gas tube 105 is also coupled to the mask system 103. The gas tube 105 further includes a tube-mask connection 144 that couples the gas tube 105 to the mask system 103. Alternatively, or additionally, the mask 104 comprises the tube-mask connection 144. For example, the tube-mask connection 144 comprises a tube-mask opening 144.

The gas tube 105 can carry the gas 107 between the robot base 116 and the mask system 103 through the tube-base connection 130.

The mask system 103 can comprise the mask 104 configured to distribute the gas 107 to the user 109. The mask system 103 can be removed from the flange 115, or the flange kinematic mount 119, for example, for one or more of cleaning, sterilizing, sanitizing, and replacing, and the like.

Figure 1B:
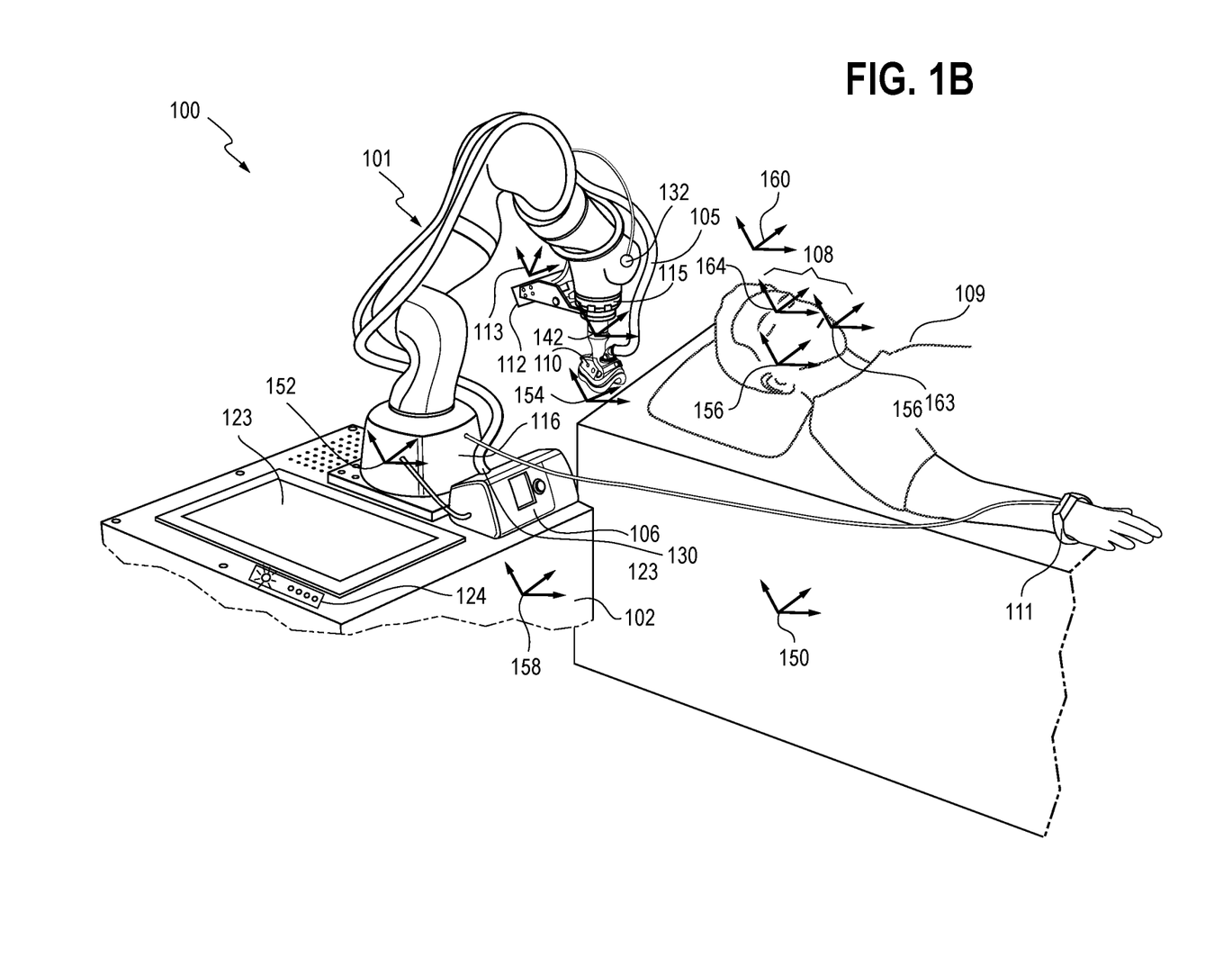
FIG. 1B is a drawing of a coordinate frame system usable with the robotic ventilation system.

FIG. 1B shows key coordinate frames of the robotic ventilation system. The coordinate frames include a world coordinate frame 150, a robot base coordinate frame 152, the flange kinematic mount coordinate frame 142, the tracking system coordinate frame 113, a mask system coordinate frame 154, a face coordinate frame 156, a system base coordinate frame 158, and a ready coordinate frame 160. These frames can represent spatial relationships and can be stored in the database 128.

The world coordinate frame 150 represents an environment reference. For example, the world coordinate frame 150 defines a common reference for all other coordinate frames.

The robot base coordinate frame 152 represents a spatial reference for the robot base 116. For example, the robot base coordinate frame 152 can be defined with respect to the robot base 116.

The flange kinematic coordinate frame 142 represents a flange 115 reference. For example, the flange kinematic coordinate frame 142 can be defined with respect to the flange 115.

The tracking system coordinate frame 113 represents a tracking system reference. For example, the tracking system coordinate frame 113 can be defined with respect to tracking system 112, and points in the tracking system coordinate frame 113 are relative to the tracking system 112.

The mask system coordinate frame 154 represents a mask reference. For example, the mask system coordinate frame 154 can be defined with respect to the mask 104.

For example, the tracking system 112 can determine the mask system coordinate frame 154 based on one or more of the mask features and a fiducial marker 110. The tracking system 112 can determine a spatial relationship of the mask system coordinate frame 154 with respect to the tracking system controller frame 113. The tracking system 112 can store the mask system coordinate frame 154 in the database 128.

The face 108 of the user 109 is represented with a face coordinate frame 156. For example, the face coordinate frame 156 can be defined with respect to a face fiducial coordinate frame 163. For example, the face coordinate frame 156 can be defined with respect to a face feature coordinate frame 164. For example, the face coordinate frame 156 can be a function of a pose of the face 108 of the user 109. For example, the face coordinate frame 156 can be defined with respect a pose of the face 108 of the user 109 at a particular point in time. For example, the face coordinate frame 156 can change as the pose of the face 108 of the user 109 changes. For example, the face coordinate frame 156 can be identical to the face fiducial coordinate frame 163. For example, the face coordinate frame 156 can comprise the face feature coordinate frame 164. The tracking system 112 can determine a transform between the face coordinate frame 156 and the mask system coordinate frame 154.

For example, the tracking system 112 can determine the face coordinate frame 156 based on one or more of a facial feature (not shown in FIG. 1B) and the fiducial marker 110. The tracking system 112 can store the face coordinate frame 156 in the database 128.

For example, the face feature coordinate frame 164 can be defined by a facial feature (not shown in FIG. 1B) of the user 109. For example, the face feature coordinate frame 164 can be a function of the pose of a face feature (not shown in FIG. 1B) of the user 109. For example, the face feature coordinate frame 164 can be defined with respect to a pose of a face feature (not shown in FIG. 1B) of the user 109 at a particular point in time. For example, the face feature coordinate frame 164 can change with respect to the tracking system 112 as the pose of the face 108 of the user 109 changes.

For example, the tracking system 112 can determine the face coordinate frame 156 based on one or more of the face feature coordinate frame 164 and the face fiducial coordinate frame 163. For example, the tracking system 112 can determine the face feature coordinate frame 164. Alternatively, or additionally, the tracking system 112 can determine the face fiducial coordinate frame 163. Alternatively, or additionally, the tracking system 112 can determine the face coordinate frame 156. For example, the tracking system 112 can determine the face coordinate frame 156 based on one or more of the determined/defined face feature coordinate frame 164 and the determined/defined face fiducial coordinate frame 163. For example, the tracking system 112 can access the face feature coordinate frame 164 in the database 128. Alternatively, or additionally, the tracking system 112 can access the face fiducial coordinate frame 163 in the database 128. Alternatively, or additionally, the tracking system 112 can determine the face coordinate frame 156. For example, the tracking system 112 can determine the face coordinate frame 156 based on one or more of the face feature coordinate frame 164 and the face fiducial coordinate frame 163.

One or more of the face coordinate frame 156, the face fiducial coordinate frame 163 and the face feature coordinate frame 164 can be tracked by the tracking system 112. The controller 122 can use the one or more of the face coordinate frame 156, the face fiducial coordinate frame 163 and the face feature coordinate frame 164 as a spatial reference to do one or more of correctly locate the mask 104 and place the mask 104 on the face 108 of the user 109.

The system base coordinate frame 158 represents a system base reference. For example, the system base coordinate frame 158 can be defined with respect to the robot base 116. For example, points in the system base coordinate frame 158 are defined relative to the robot base 116.

For example, the ready coordinate frame 160 represents a taught reference that can be learned and maintained. For example, the ready coordinate frame 160 can be defined with respect to the mask 104. For example, the ready coordinate frame 160 can be defined when the face 108 of the user 109 is in the field of view of the tracking system 112. In this example, the system controller 122 can wait for the user 109 to enter a requisite sleep state.

The tracking system 112 can determine spatial relationships between two or more bodies in space. For example, the tracking system 112 can determine a spatial relationship between a first body in space and a second body in space. For example, the tracking system 112 can define a first coordinate frame for the first body in space. For example, the tracking system 112 can define a second coordinate frame for the second body in space. The tracking system 112 can then determine a transform between the first coordinate frame and the second coordinate frame, the transform describing a spatial relationship between the first body in space and the second body in space. The tracking system 112 can determine a transform between the face coordinate frame 156 and the mask system coordinate frame 154. The tracking system 112 can use chaining to determine the spatial relationships. The tracking system 112 can store the transform between the first coordinate frame and the second coordinate frame in the database 128.

Figure 2:
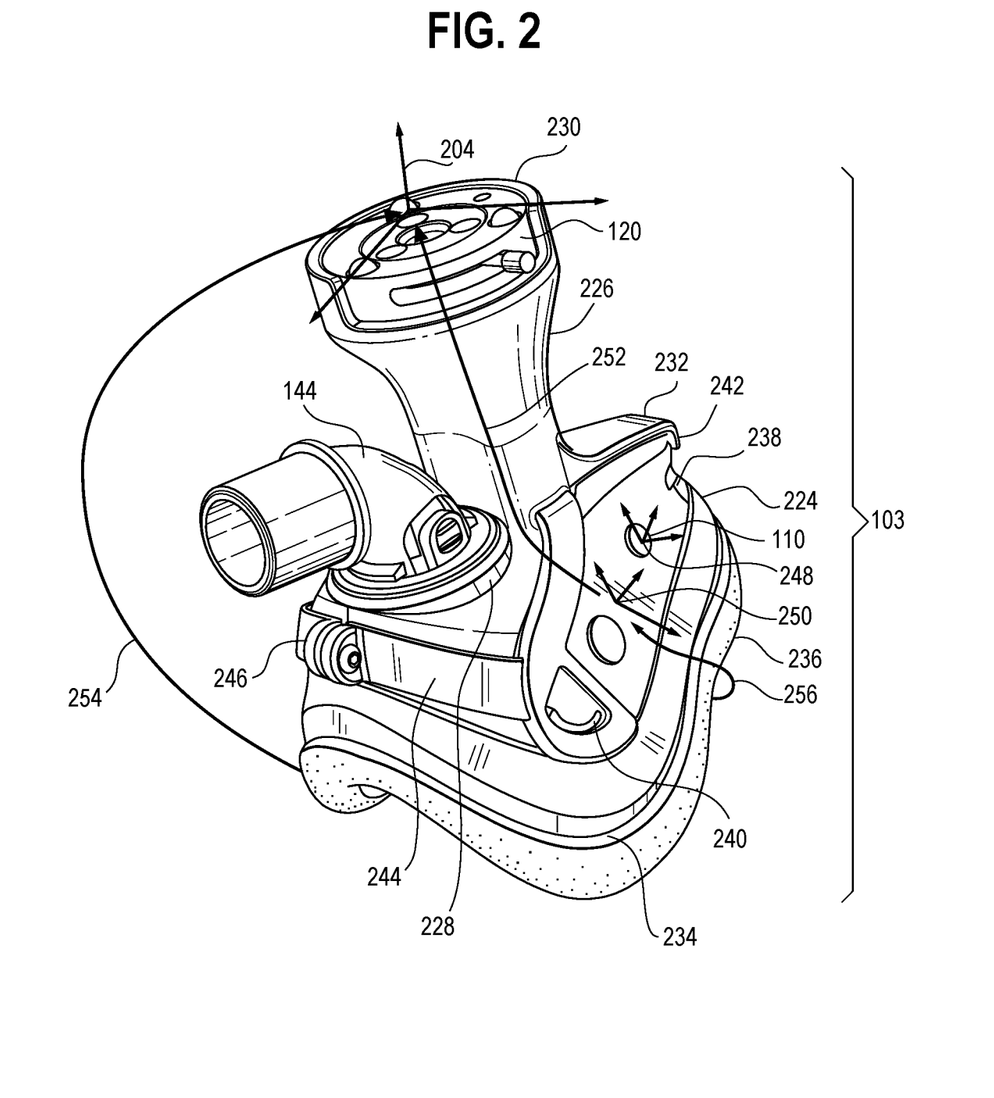
FIG. 2 is a drawing of a mask system of the robotic ventilation system.

FIG. 2 is a drawing of the mask system 103 of the robotic ventilation system 100. The mask system 103 again comprises the mask 104 and the fiducial marker 110. As depicted, the mask 104 further comprises the tube-mask connection 144.

As depicted, the mask system 103 further comprises a housing 224. The mask system 103 further comprises a facial interface stem 226, the facial interface stem 226 configured to offset the mask 104 to provide clearance for the mask-tube connection 144. The mask 104 further comprises a mask stem 228 configured to protrude through a mask stem opening 229 to enable clamping. The facial interface stem 226 comprises a stem-flange connection 230 through which the facial interface stem 226 couples to the flange 115. For example, the stem-flange connection 230 comprises a stem-flange opening 230. Optionally, a single connection (not shown) comprises both the tube-mask connection 144 and the stem-flange connection 230.

The mask system 103 further comprises a mask mounting feature 232 usable to mount the mask 104 to the facial interface stem 226. Preferably, but not necessarily, the mask mounting feature 232 is rigidly fixed to the mask stem 228. The mask mounting feature 232 is usable to locate the mask 104 with respect to the flange 115. Alternatively, or additionally, the mask mounting feature 232 is usable to orient the mask 104 with respect to the flange 115. The mask mounting feature 232 comprises one or more of the mask system mounting feature 232, a magnetic mask system mounting feature 232, a mechanical mask mounting feature, and a clamp-on mask mounting feature.

The mask 104 can be coupled to the flange 115 via the mask mounting feature 232. For example, the mask mounting feature 232 can engage with the robot mounting feature 138. The mask mounting feature 232 allows for a repeatable mechanical connection between the mask 104 and the flange 115.

The mask 104 can further comprise a contact edge 234. The contact edge 234 comprises a mask seal 236. The mask seal 236 covers the contact edge 234. The contact edge 234 can be substantially rigid. The mask seal 236 can comprise one or more of an inflatable bladder and a soft deformable material. The mask seal 236 is configured to conform to the face of the user. The mask seal 236 is further configured to facilitate formation of an effective seal against the face of the user during use. The mask seal 236 ensures secure delivery to the user of correctly pressurized gas 107.

Optionally, the mask 104 and the facial interface stem 226 are separable components. In other words, the mask 104 and the mask stem 228 can be detached from one another. The mask 104 and the mask stem 228 can be coupled using a coupling mechanism.

The mask 104 further comprises a groove 238 configured to engage with the mask mounting feature 232. Optionally, and as depicted, the mask 104 can further include a wing 240 configured to engage with the mask mounting feature 232. As depicted, the wing 240 extends outward from the mask 104. The mask system 103 further comprises a protrusion 242 configured to engage with the groove 238. Optionally, and as depicted, the facial interface stem 226 further comprises a clamping portion 244 configured to clamp the mask stem 228. Optionally, and as depicted, the facial interface stem 226 further comprise a screw portion 246 usable to do one or more of clamp the mask stem 228 and further clamp the mask stem 228. The screw portion 246 is configured to clamp the mask stem 228 via tightening of the screw portion 246.

If the screw portion 246 is engaged to tighten the contact between the clamping portion 244 and the wing 240, the mask stem 228 and the mask 104 can be effectively coupled together. If the screw portion, is disengaged to loosen the contact between the clamping portion 244 and the wings 240, the mask stem 228 and the mask 104 can be separated from one another by disengaging the contact between the clamping portions 222 and the wings 218, and by disengaging the protrusion 242 from the groove 238.

The fiducial marker 110 comprises a fiducial marker coordinate frame 248. The fiducial marker 110 can be tracked by the tracking system 112. The fiducial marker 110 can serve as a tracking reference for the tracking system 112. The fiducial marker coordinate frame 248 can be defined by features of the fiducial marker 110. For example, the open source ArUco library (Universitario de Rabanales, University of Córdoba, 14071, Córdoba, Spain) (www.uco.es) includes numerous fiducial marker designs with coordinate frames defined from the design features.

A mask system fiducial marker coordinate frame 250 can be defined with respect to the mask system coordinate frame 154. Alternatively, or additionally, the mask system fiducial marker coordinate frame 250 can be defined with respect to the fiducial marker coordinate frame 248. For example, a measuring tool can be used such as the Gauge Max Faro Arm, manufactured by Faro Technologies, Inc. of Lake Mary, Florida (www.faro.com). Alternatively, or additionally, the spatial relationship 250 may be incorporated into the mask 104 during construction of the mask 104. The mask system coordinate frame can be stored in the database.

A spatial relationship 252 of the fiducial marker coordinate frame 248 can be defined with respect to the mask system coordinate frame 154. Alternatively, or additionally, the spatial relationship 252 may be incorporated into the mask system 103 during construction.

A spatial relationship 254 of the mask seal 236 can be defined with respect to the mask system coordinate frame 154. Alternatively, or additionally, the spatial relationship 254 may be incorporated into the mask system 103 during construction.

A spatial relationship 256 of the fiducial marker coordinate 248 frame can be defined with respect the mask seal 236. Alternatively, or additionally, the spatial relationship 230 may be incorporated into the mask 104 during construction of the mask 104.

Figure 3:
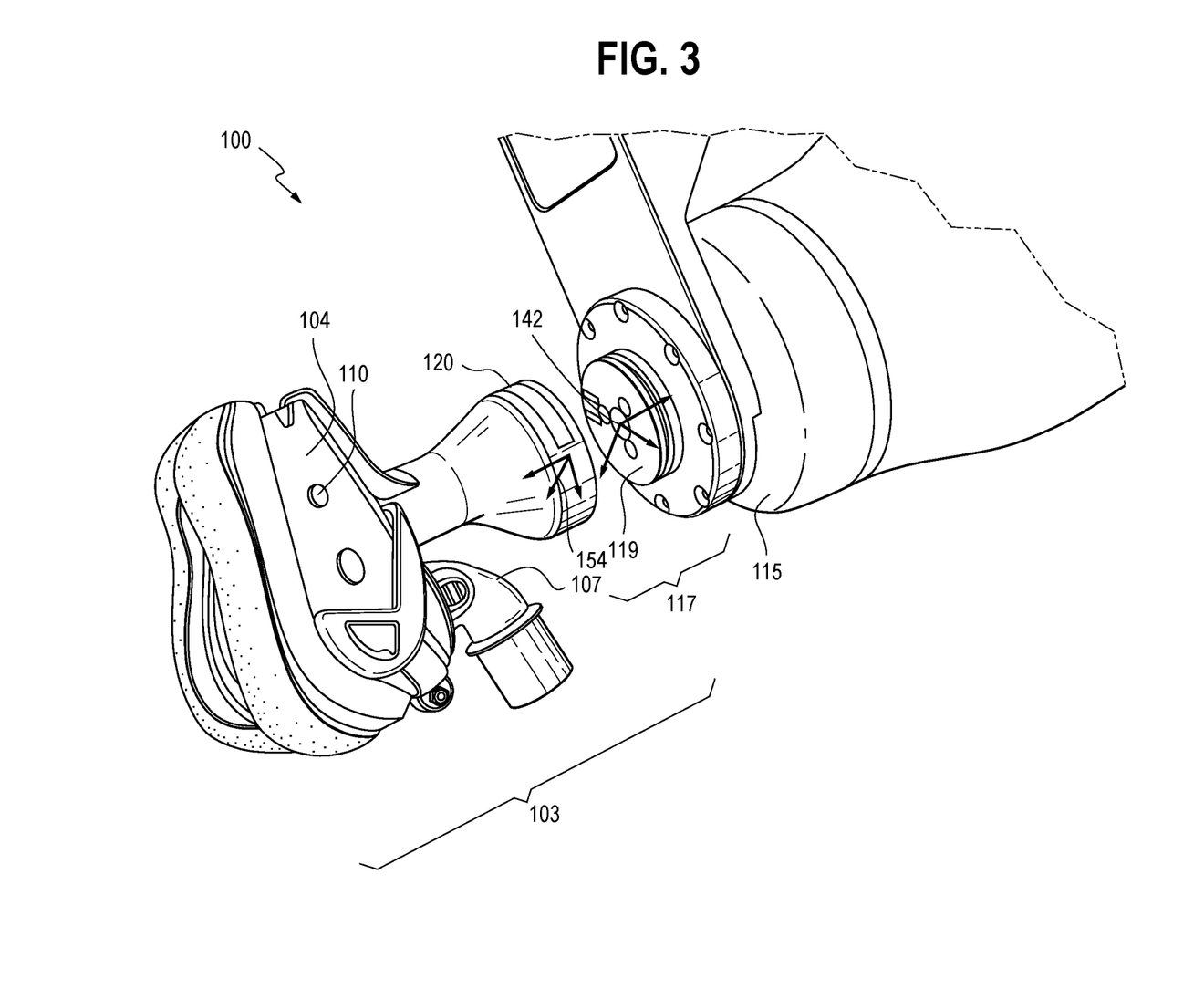
FIG. 3 is a drawing of a detail of the robotic ventilation system, showing the mask system attaching to a flange via a kinematic mount.

FIG. 3 is a drawing of a detail of the robotic ventilation system 100, showing the mask system 103 attaching to the flange 115 via the kinematic mount 117.

FIG. 3 shows the mask system 103 comprising the mask 104 and the fiducial marker 110. The kinematic mount 117 again comprises the flange kinematic mount 119 and the mask system kinematic mount 120. FIG. 3 also shows the arm 114 that is distal from the robot base (not shown in this figure; item 116 in FIG. 1A). The arm 114 comprises the flange 115. The flange 115 in turn comprises the flange kinematic mount 119. Preferably, but not necessarily, the flange kinematic mount 119 is rigidly fixed relative to the flange 115. The flange kinematic mount 119 can engage with the mask system kinematic mount 120 to do one or more of locate and orient the mask 104 with respect to the flange 115.

The flange kinematic mount 119 comprises a flange kinematic mount coordinate frame 142. When coupled, there can be a fixed spatial relationship between the flange coordinate frame 142 and the mask system kinematic mount coordinate frame 154. The flange kinematic mount 119 allows for creation of a repeatable mechanical connection between the mask system 103 and the flange 115 such that when the mask system 103 is removed from a first mask position and then reattached, the mask system 103 goes back into the same first mask position with respect to the flange 115 in a repeatable, predictable manner. Alternatively, or additionally, the mask system 103 that is removed can be a distinct mask system 103 from the mask system that is later reattached.

Figure 4:
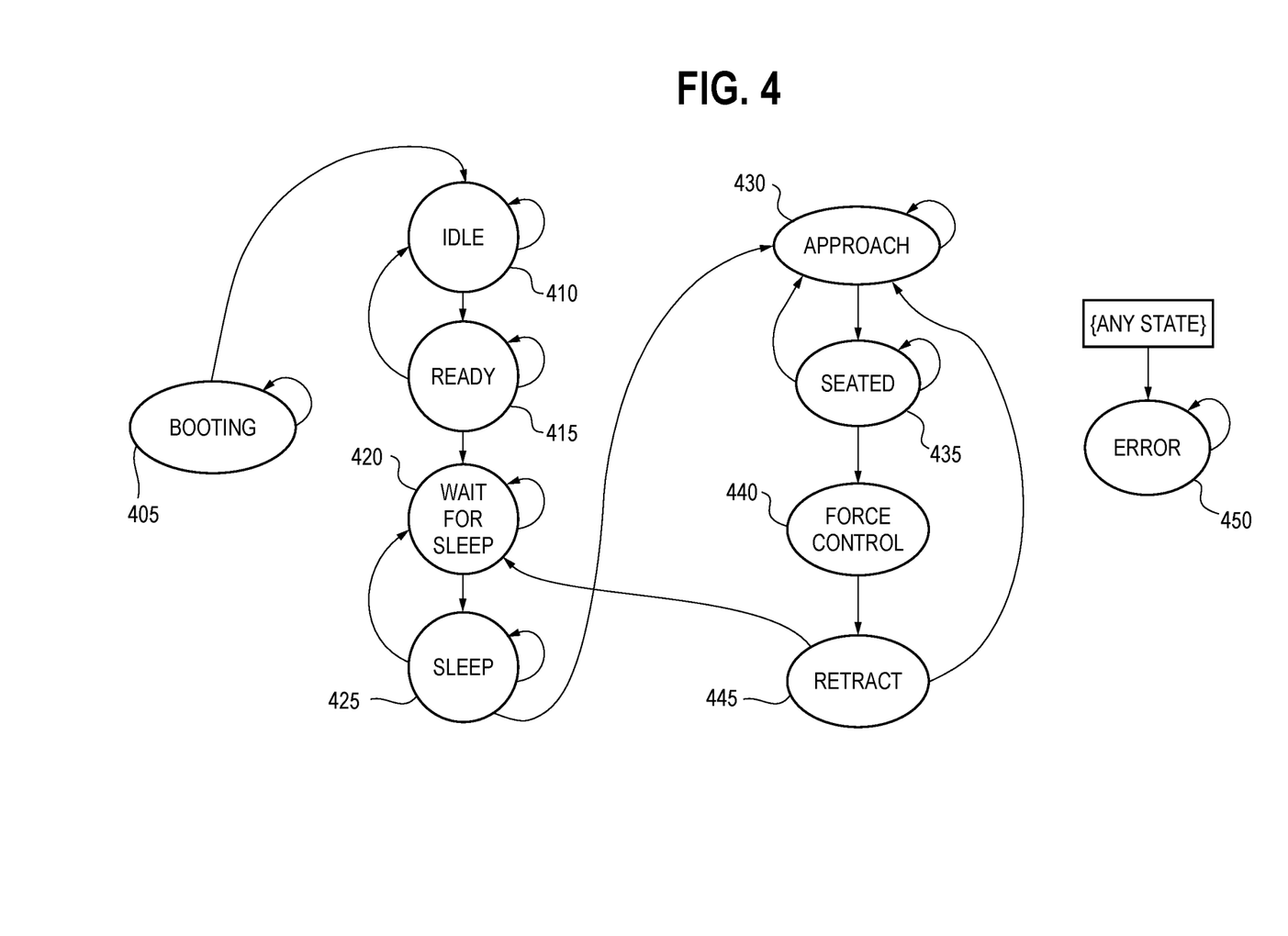
FIG. 4 is a drawing of a state machine comprising one or more states that the robotic ventilation system can assume.

FIG. 4 is a drawing of a state machine 400 comprising one or more states that the system can assume. The state machine 400 includes one or more of a booting state 405 in which the system boots up, the booting state 405 operably connected to itself, an idle state 410 in which the system rests, the idle state 410 operably connected to the booting state 405, the idle state 410 operably connected to itself, a ready state 415 in which the system readies itself for action, the ready state 415 operably connected to the idle state 410, the ready state operably connected to itself, a wait for sleep state 420 in which the system awaits a user transition from one sleep state to another sleep state, the wait for sleep state 420 operably connected to the ready state 415, the wait for sleep state 420 operably connected to itself, a sleep state 425 in which the user sleeps, the sleep state 425 operably connected to the wait for sleep state 420, the sleep state 425 operably connected to itself, an approach state 430 in which the system approaches the user, the approach state 430 operably connected to the sleep state 425, the approach state 430 operably connected to itself, a seated state 435 in which the system seats the mask on the user's face, the seated state 435 operably connected to the approach state 430, the seated state 435 operably connected to itself, a force control state 440 in which a force exerted on the face by the mask is controlled, the force control state 440 operably connected to the seated state 435, and a retract state 445 in which the system transitions the mask pose from the seated pose to the ready pose, the retract state 445 operably connected to the wait for sleep state 420. The state machine 400 preferably further comprises an error state 450 in which the system responds to a system error, the error state 450 operably connected to one or more of the booting state 405, the idle state 410, the ready state 415, the wait for sleep state 420, the sleep state 425, the approach state 430, the seated state 435, the force control state 440, the retract state 445, and the error state 450. Preferably, but not necessarily, and as depicted, the error state 450 is operably connected to each of the booting state 405, the idle state 410, the ready state 415, the wait for sleep state 420, the sleep state 425, the approach state 430, the seated state 435, the force control state 440, the retract state 445, and the error state 450. Preferably, but not necessarily, and as depicted, the state machine 400 comprises each of the booting state 405, the idle state 410, the ready state 415, the wait for sleep state 420, the sleep state 425, the approach state 430, the seated state 435, the force control state 440, the retract state 445, and the error state 450.

In the booting state 405, the system boots one or more system components. For example, the system boots one or more of the ventilator, the robot, the tracking system, and the biometric sensor system. For example, booting comprises transitioning the booted component from a sleep state to an idle state.

In the idle state 410, the system idles one or more system components. For example, the system idles one or more of the ventilator, the robot, the tracking system, and the biometric sensor system. Alternatively, or additionally, in the idle state, the system sets the pose of the mask to the idle pose. For example, the user initiates the transition from the idle state 410 to the ready state 415 using the display.

In the ready state 415, the system does one or more of estimate the sleep state of the user and wait for the user to transition from one sleep state to another sleep state. For example, the system waits for the user to transition from a wakefulness state to one or more of a stage 1 non-REM sleep state, a stage 2 non-REM sleep state, a stage 3 non-REM sleep state, and an REM sleep state. For example, the system sets the mask pose to the ready pose. For example, the user initiates the transition from the ready state to the wait for sleep state 420 using the display.

In the wait for sleep state 420, the system estimates the sleep state of the user. Alternatively, or additionally, the system waits for the user to transition from one sleep state to another sleep state. For example, the system waits for the user to transition from a stage 1 non-REM sleep state to one or more of a stage 2 non-REM sleep state, a stage 3 non-REM sleep state, and an REM sleep state. Alternatively, or additionally, the system waits for the user to transition from a stage 2 non-REM sleep state to one or more of a stage 3 non-REM sleep state and an REM sleep state. Alternatively, or additionally, the system waits for the user to transition from a stage 3 non-REM sleep state to an REM sleep state. For example, the system sets the mask pose to the ready pose. For example, the system can abort the transition from the wait for sleep state 420 to the sleep state 425 based at least in part on input from the user, for example using the display.

In the sleep state 425, the system determines whether the estimated sleep state of the user comprises a requisite sleep state The requisite sleep state may be predetermined by the user. Alternatively, or additionally, the requisite sleep state may be determined by the system. For example, the requisite sleep state may be determined by the system. For example, the requisite sleep state may be calculated by the system. For example, the requisite sleep state comprises one or more of a wakeful state, a stage 1 non-rapid eye movement (non-REM) sleep state, a stage 2 non-REM sleep state, a stage 3 non-REM sleep state, and an REM sleep state, Alternatively, or additionally, the system determines whether the estimated sleep state of the user is stable. For example, the system transitions from the sleep state 425 to the approach state 430 if the system determines that the estimated sleep state of the user is the requisite sleep state and if the system also determines that the estimated sleep state of the user is stable. For example, the system transitions from the sleep state 425 to the wait for sleep state 420 if the system determines one or more of that the estimated sleep state of the user is not the requisite sleep state and that the estimated sleep state of the user is not stable.

In the approach state 430, the system transitions the mask pose from the ready pose to the seated pose.

In the seated state 435, the system sets the mask pose to the seated pose. Alternatively, or additionally, the system supplies gas to the user. For example, the system transitions from the seated state 435 to the force control state 440 if the system is able to successfully set the mask pose to the seated pose. For example, the system transitions from the seated state 435 to the approach state 430 if the system is not able to successfully set the mask pose to the seated pose.

In the force control state 440, the system operates the mask such that the mask maintains one or more of the seated pose and an appropriate contact force. Alternatively, or additionally, the system supplies gas to the user. For example, the system continuously maintains one or more of the seated pose and the appropriate contact force even while the user moves. Preferably, but not necessarily, the system continuously maintains both the seated pose and the appropriate contact force even while the user moves.

The system transitions from the force control state 440 to the retract state 445 if the mask is unable to maintain one or more of the appropriate contact force and the seated position. Preferably, but not necessarily, the system transitions from the force control state 440 to the retract state 445 if the mask is unable to maintain both the appropriate contact force and the seated position. If the mask is not able to maintain both the appropriate contact force and the seated position, the system can alert the user, for example, using the display.

In the retract state 445, the system transitions the mask pose from the seated pose to the ready pose. For example, the system transitions from the retract state 445 to the wait for sleep state 420 if the system estimates the state of the user as one or more of a stage 1 non-REM sleep state, a stage 2 non-REM sleep state, and a stage 3 non-REM sleep state. For example, the system transitions from the retract state 445 to the approach state 430 if the system estimates the state of the user as one or more of a stage 2 non-REM sleep state, a stage 3 non-REM sleep state, and an REM sleep state.

In the error state 450, the system transitions the mask pose to one or more of the idle pose and the ready pose.

Figure 5:
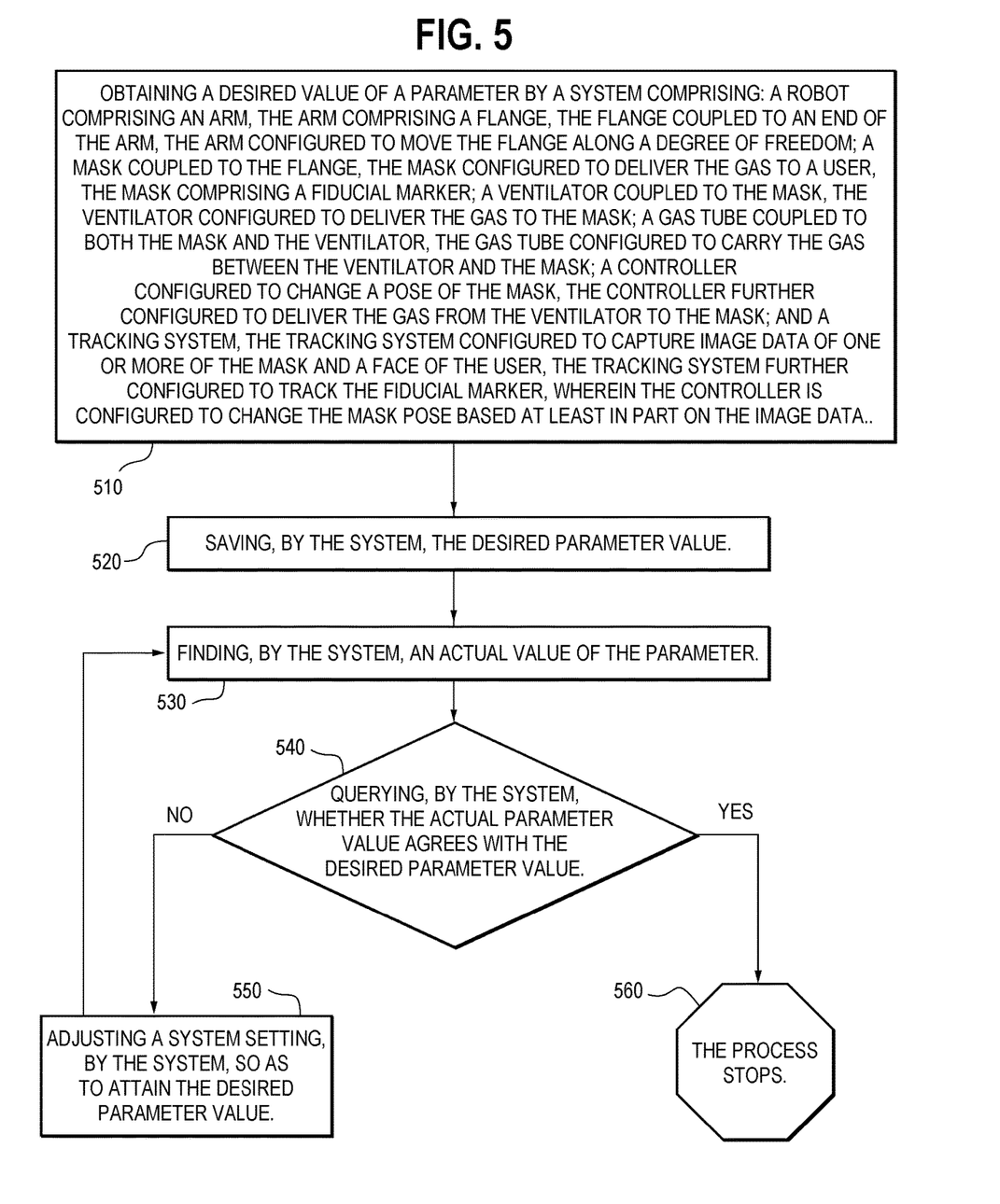
FIG. 5 is a flow chart of a robotic ventilation method for automatic delivery of breathable gas.

FIG. 5 is a flow chart of a method 500 for using feedback control to assure accurate mask placement with a robotic ventilation system including a mask having a robotic mounting feature and a tracking fiducial.

The order of the steps in the method 500 is not constrained to that shown in FIG. 5 or described in the following discussion. Several of the steps could occur in a different order without affecting the final result.

In step 510, a desired value of a parameter is obtained using a system comprising: a robot comprising an arm, the arm comprising a flange, the flange coupled to an end of the arm, the arm configured to move the flange along a degree of freedom; a mask coupled to the flange, the mask configured to deliver gas to a user; a ventilator coupled to the mask, the ventilator configured to deliver the gas to the mask; a gas tube coupled to both the mask and the ventilator, the gas tube configured to carry gas between the ventilator and the mask; a controller configured to change a pose of the mask, the controller further configured to control the delivery of the gas from the ventilator to the user; and a tracking system, the tracking system configured to capture image data of one or more of the mask and a face of the user, the tracking system comprising an illumination system configured to emit light in a field of view of the tracking system, wherein the controller is configured to change the mask pose based at least in part on the image data, obtaining a desired value of a parameter. For example, the obtaining step comprises one or more of computing the desired parameter value and receiving the desired parameter value from the user. For example, the desired parameter value comprises a range of desired parameter values.

The parameter comprises one or more of a ventilator parameter, a system parameter, and a user parameter. The parameter comprises one or more of a gas pressure, a gas temperature, a gas volume, a gas flow level, a gas leakage level, a ventilator power level, a system power level, a user heart rate, a user respiratory rate, a user temperature, a user blood oxygen saturation level, a user eye state, motion of the user or lack thereof, an estimated sleep state of the user, a sleep profile of the user, a user pulse rate, a temperature of the user, a blood oxygen saturation level of the user, an eye state of the user, a contact force of the robotic arm with respect to the user's face, a torque of the robotic arm with respect to the user's face, and a position of the robotic arm with respect to the user's face. Block 510 then transfers control to block 520.

In step 520, the system saves the desired parameter value. For example, the system saves the desired parameter value in the database. Block 520 then transfers control to block 530.

In step 530, the system finds an actual value of the parameter. For example, the system measures the actual parameter value. For example, the system receives the actual parameter value from a third party source. For example, the third party source comprises a biometric sensor. For example, the biometric sensor comprises a sleep sensor. For example, the sleep sensor comprises an Oura Ring device sold by Oura Health, Ltd. Of Oura, Finland (www.Ouraring.com). For example, the actual parameter can be one or more of an air flow rate and an air pressure value.

For example, the actual parameter value provided by the third party source comprises one or more of a user heart rate, a user respiratory rate, a user temperature, a user blood pressure, a user blood oxygen saturation level, a user eye state, motion of the user or lack thereof, an estimated sleep state of the user, a sleep profile of the user, a user pulse rate, a temperature of the user. Block 530 then transfers control to block 540.

In step 540, the system queries whether the actual parameter value agrees with the desired parameter value. If no, the process continues to step 550. If yes, the process proceeds to step 560.

In step 550, the system adjusts a system setting so as to attain the desired parameter value. For example, the system setting comprises one or more of a gas pressure, a gas temperature, a gas volume, a gas flow level, a gas leakage level, a ventilator power level, a system power level, a contact force of the robotic arm with respect to the user's face, a torque of the robotic arm with respect to the user's face, a position of the robotic arm with respect to the user's face, a torque of the ventilator motor, a speed of the ventilator motor, and a ventilator air heater current.

Optionally, the adjusting step comprises sub-steps of obtaining a revised desired value of the parameter, saving the revised desired parameter value, and adjusting the system setting so as to attain the revised desired parameter value.

The process then loops back to step 530, proceeds next to step 540, and then, and next continues with the steps of adjusting, determining, and querying until the actual parameter value agrees with the desired parameter value, at which point the process proceeds to step 560.

In step 560, the process stops.

Figure 6:
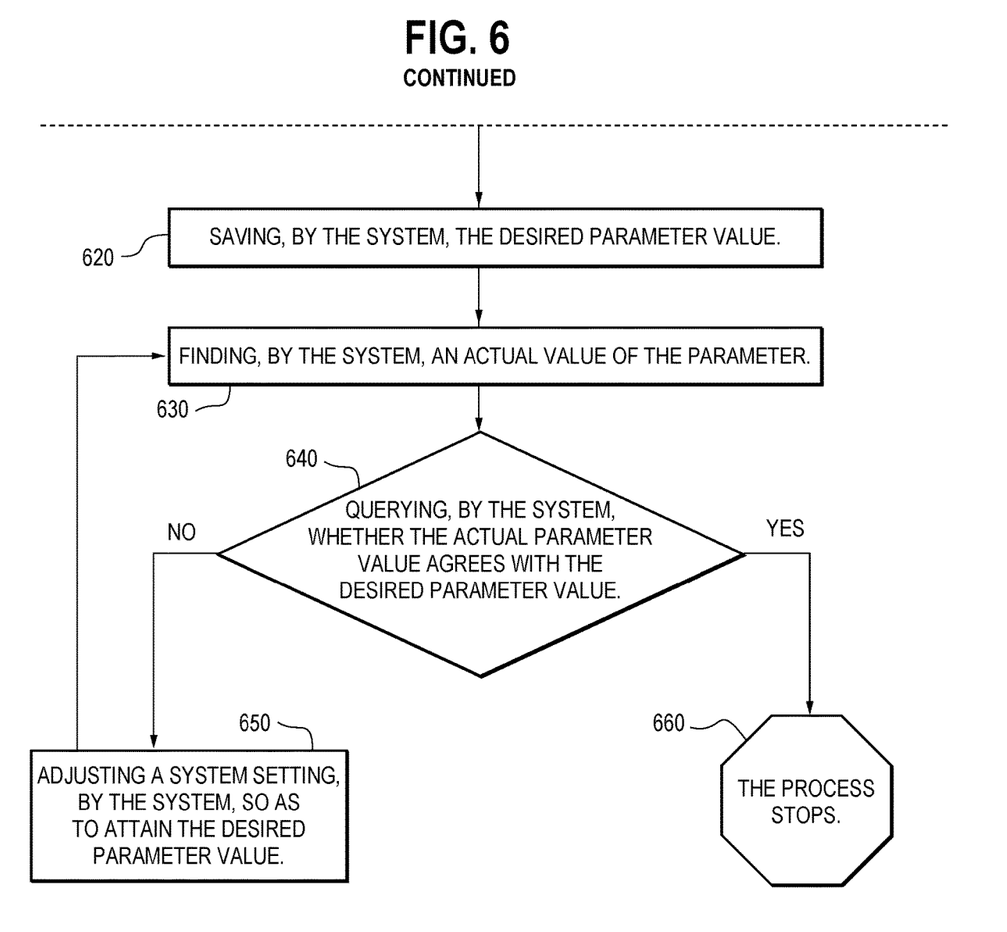
FIG. 6 is a flow chart of a robotic ventilation method for automatic delivery of breathable gas.

FIG. 6 is a flow chart of a method 600 for using feedback control to assure accurate mask placement with a robotic ventilation system including a mask having a robotic mounting feature and a tracking fiducial.

The order of the steps in the method 600 is not constrained to that shown in FIG. 6 or described in the following discussion. Several of the steps could occur in a different order without affecting the final result.

In step 610, a desired value of a parameter is obtained using a system comprising: a robot comprising an arm, the arm comprising a flange, the flange coupled to an end of the arm, the arm configured to move the flange along a degree of freedom; a mask coupled to the flange, the mask configured to deliver gas to a user; a ventilator coupled to the mask, the ventilator configured to deliver the gas to the mask, wherein following a start of delivery of pressurized gas to the user, the system commands the robotic arm to maintain both an appropriate contact force with respect to a face of the user face and an appropriate position with respect to the user's face, wherein following movement of the face of the user, the robotic arm is configured to do one or more of move its location and change the contact force to maintain both an appropriate contact force with respect to a face of the user face and an appropriate position with respect to the user's face, wherein following a failure of the system to maintain both an appropriate contact force and an appropriate position, the system is configured to retract the robotic arm so as to move the mask away from the face of the user, wherein following retraction of the robotic arm, if the user is in a requisite sleep state, the system is configured to move the robotic arm toward the face of the user, wherein following retraction of the robotic arm, if the user is awake, the system is configured to go into a mode in which it awaits entry into a requisite sleep state by the user, wherein following the entry into the requisite sleep state by the user, the system moves the robotic arm toward the face of the user; a gas tube coupled to both the mask and the ventilator, the gas tube configured to carry gas between the ventilator and the mask; a controller configured to change a pose of the mask, the controller further configured to control the delivery of the gas from the ventilator to the user, wherein the controller is further configured to change the mask pose based on one or more of the image data and an estimated sleep state of the user, wherein the estimated sleep state comprises one or more of a requisite sleep state and an estimation of stability of the user's sleep state, wherein the system transitions from the sleep state to an approach state if the system determines the estimated sleep state of the user is the requisite sleep state and if the system further determines that the estimated sleep state of the user is stable, wherein the system transitions from the sleep state to a wait for sleep state in which the system waits if the system determines one or more of that the estimated sleep state of the user is not the requisite sleep state and that the estimated sleep state of the user is not stable; a tracking system, the tracking system configured to capture image data of one or more of the mask and the face of the user, the tracking system comprising an illumination system configured to emit light in a field of view of the tracking system; a biometric sensor system, the biometric sensor system comprising a biometric sensor, wherein the controller is configured to change the mask pose based at least in part on biometric data from the biometric sensor system; and an image processing block configured to process the image data, the image processing block further configured to identify a face feature point, wherein the face feature point comprises one or more of an eye center point, a nose center point, a mouth lateral point, and a mouth center point, wherein the system moves the robotic arm toward the face of the user after the face feature point is identified. For example, the obtaining step comprises one or more of computing the desired parameter value and receiving the desired parameter value from the user. For example, the desired parameter value comprises a range of desired parameter values.

The parameter comprises one or more of a ventilator parameter, a system parameter, and a user parameter. The parameter comprises one or more of a gas pressure, a gas temperature, a gas volume, a gas flow level, a gas leakage level, a ventilator power level, a system power level, a user heart rate, a user respiratory rate, a user temperature, a user blood oxygen saturation level, a user eye state, motion of the user or lack thereof, an estimated sleep state of the user, a sleep profile of the user, a user pulse rate, a temperature of the user, a blood oxygen saturation level of the user, an eye state of the user, a contact force of the robotic arm with respect to the user's face, a torque of the robotic arm with respect to the user's face, and a position of the robotic arm with respect to the user's face. Block 610 then transfers control to block 620.

In step 620, the system saves the desired parameter value. For example, the system saves the desired parameter value in the database. Block 620 then transfers control to block 630.

In step 630, the system finds an actual value of the parameter. For example, the system measures the actual parameter value. For example, the system receives the actual parameter value from a third party source. For example, the third party source comprises a biometric sensor. For example, the biometric sensor comprises a sleep sensor. For example, the sleep sensor comprises an Oura Ring device sold by Oura Health, Ltd. Of Oura, Finland (www.Ouraring.com). For example, the actual parameter can be one or more of an air flow rate and an air pressure value.

For example, the actual parameter value provided by the third party source comprises one or more of a user heart rate, a user respiratory rate, a user temperature, a user blood pressure, a user blood oxygen saturation level, a user eye state, motion of the user or lack thereof, an estimated sleep state of the user, a sleep profile of the user, a user pulse rate, a temperature of the user. Block 630 then transfers control to block 640.

In step 640, the system queries whether the actual parameter value agrees with the desired parameter value. If no, the process continues to step 650. If yes, the process proceeds to step 660.

In step 650, the system adjusts a system setting so as to attain the desired parameter value. For example, the system setting comprises one or more of a gas pressure, a gas temperature, a gas volume, a gas flow level, a gas leakage level, a ventilator power level, a system power level, a contact force of the robotic arm with respect to the user's face, a torque of the robotic arm with respect to the user's face, a position of the robotic arm with respect to the user's face, a torque of the ventilator motor, a speed of the ventilator motor, and a ventilator air heater current.

Optionally, the adjusting step comprises sub-steps of obtaining a revised desired value of the parameter, saving the revised desired parameter value, and adjusting the system setting so as to attain the revised desired parameter value.

The process then loops back to step 630, proceeds next to step 640, and then, and next continues with the steps of adjusting, determining, and querying until the actual parameter value agrees with the desired parameter value, at which point the process proceeds to step 660.

In step 660, the process stops.

The foregoing description of the embodiments of the disclosure has been presented for the purpose of illustration; it is not intended to be exhaustive or to limit the disclosure to the precise form disclosed. Persons skilled in the relevant art can appreciate that many modifications and variations are possible in light of the above disclosure.

Any steps, operations, or processes described herein may be performed or implemented with one or more hardware or software modules, alone or in combination with other devices. In some embodiments, a software module is implemented with a computer program product including a computer-readable medium containing computer program code, which can be executed by a computer processor for performing any or all of the steps, operations, or processes described.

Embodiments of the disclosure can also relate to an apparatus for performing the operations herein. This apparatus can be specially constructed for the required purposes, and/or it can include a general-purpose computing device selectively activated or configured by a computer program stored in the computer. Such a computer program can be stored in a non-transitory, tangible computer readable storage medium, or any type of media suitable for storing electronic instructions, which can be coupled to a computer system bus. Furthermore, any computing systems referred to in the specification can include a single processor or can be architectures employing multiple processor designs for increased computing capability.

Throughout this specification, although individual operations of one or more methods are illustrated and described as separate operations, one or more of the individual operations may be performed concurrently, and nothing requires that the operations be performed in the order illustrated. One or more operations of one or more methods can be optional. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Finally, the language used in the specification has been principally selected for readability and instructional purposes, and it may not have been selected to delineate or circumscribe the disclosure. It is therefore intended that the scope of the disclosure be limited not by this detailed description, but rather by any claims that issue on an application based hereon. Accordingly, the disclosure of the embodiments of the disclosure is intended to be illustrative, but not limiting, of the scope of the disclosure, which is set forth in the following claims.

The invention claimed is:

1. A robotic ventilation method for automatic delivery of breathable gas, comprising:
   obtaining a desired value for a parameter relevant to the automatic delivery of the breathable gas using a system comprising:
      a robot comprising an arm, the arm comprising a flange, the flange coupled to an end of the arm, the arm configured to move the flange along a degree of freedom;
      a mask coupled to the flange, the mask configured to deliver gas to a user;
      a ventilator coupled to the mask, the ventilator configured to deliver the gas to the mask;
      a gas tube coupled to both the mask and the ventilator, the gas tube configured to carry gas between the ventilator and the mask;
      a controller configured to change a pose of the mask, the controller further configured to control the delivery of the gas from the ventilator to the user;
      a tracking system, the tracking system configured to capture image data of one or more of the mask and a face of the user, wherein the controller is configured to change the mask pose based at least in part on the image data; and
      a sensor, the sensor configured to sense one or more of a parameter value, wherein the controller is configured to change the mask pose based on the parameter value;
   saving, by the system, the desired parameter value;
   finding, by the system, an actual value of the parameter;
   querying, by the system, whether the actual parameter value agrees with the desired parameter value;
   determining, by the system, that the actual parameter value does not agree with the desired parameter value;
   adjusting, by the system, a system setting so as to attain the desired parameter value;
   querying, by the system, whether the actual revised parameter value agrees with the desired parameter value; and
   repeating, by the system, the steps of determining, adjusting, and querying whether the actual revised parameter value agrees with the desired parameter value until the actual revised parameter value agrees with the desired parameter value, wherein the ventilator is configured to automatically deliver the breathable gas to the user after detecting a state of the user, wherein the state of the user comprises a requisite sleep state of the user.

2. A robotic ventilation method for automatic delivery of breathable gas, comprising:
   obtaining a desired value for a parameter relevant to the automatic delivery of the breathable gas using a system comprising:

a robot comprising an arm, the arm comprising a flange, the flange coupled to an end of the arm, the arm configured to move the flange along a degree of freedom;

a mask coupled to the flange, the mask configured to deliver gas to a user;

a ventilator coupled to the mask, the ventilator configured to deliver the gas to the mask;

a gas tube coupled to both the mask and the ventilator, the gas tube configured to carry gas between the ventilator and the mask;

a controller configured to change a pose of the mask, the controller further configured to control the delivery of the gas from the ventilator to the user;

a tracking system, the tracking system configured to capture image data of one or more of the mask and a face of the user, wherein the controller is configured to change the mask pose based at least in part on the image data; and a sensor, the sensor configured to sense one or more of a parameter value, wherein the controller is configured to change the mask pose based on the parameter value;

saving, by the system, the desired parameter value;

finding, by the system, an actual value of the parameter;

querying, by the system, whether the actual parameter value agrees with the desired parameter value;

determining, by the system, that the actual parameter value does not agree with the desired parameter value;

adjusting, by the system, a system setting so as to attain the desired parameter value;

querying, by the system, whether the actual revised parameter value agrees with the desired parameter value; and repeating, by the system, the steps of determining, adjusting, and querying whether the actual revised parameter value agrees with the desired parameter value until the actual revised parameter value agrees with the desired parameter value, wherein the ventilator is configured to automatically deliver the breathable gas to the user after detecting a state of the user, wherein the state of the user comprises a requisite sleep state of the user, wherein the requisite sleep state is one or more of predetermined by the user and is determined by the system, wherein the system delivers the breathable gas to the user after the user falls asleep.

3. A robotic ventilation method for automatic delivery of breathable gas, comprising:

obtaining a desired value for a parameter affected by the automatic delivery of the breathable gas using a system comprising:

a robot comprising an arm, the arm comprising a flange, the flange coupled to an end of the arm, the arm configured to move the flange along a degree of freedom;

a mask coupled to the flange, the mask configured to deliver gas to a user;

a ventilator coupled to the mask, the ventilator configured to deliver the gas to the mask;

a gas tube coupled to both the mask and the ventilator, the gas tube configured to carry gas between the ventilator and the mask;

a controller configured to change a pose of the mask, the controller further configured to control the delivery of the gas from the ventilator to the user; and a tracking system, the tracking system configured to capture image data of one or more of the mask and a face of the user, wherein the controller is configured to change the mask pose based at least in part on the image data; and a sensor, the sensor configured to sense a parameter value, wherein the controller is configured to change the mask pose based on the parameter value;

saving, by the system, the desired parameter value;

using the system, finding an actual value of the parameter;

querying whether the actual parameter value agrees with the desired parameter value; and determining that the actual parameter value agrees with the desired parameter value, wherein the state of the user comprises a requisite sleep state of the user.

4. A robotic ventilation method for automatic delivery of breathable gas, comprising:

obtaining a desired value for a parameter relevant to the automatic delivery of the breathable gas using a system comprising:

a robot comprising an arm, the arm comprising a flange, the flange coupled to an end of the arm, the arm configured to move the flange along a degree of freedom;

a mask coupled to the flange, the mask configured to deliver gas to a user;

a ventilator coupled to the mask, the ventilator configured to deliver the gas to the mask;

a gas tube coupled to both the mask and the ventilator, the gas tube configured to carry gas between the ventilator and the mask;

a controller configured to change a pose of the mask, the controller further configured to control the delivery of the gas from the ventilator to the user;

a tracking system, the tracking system configured to capture image data of one or more of the mask and a face of the user, wherein the controller is configured to change the mask pose based at least in part on the image data; and a sensor, the sensor configured to sense one or more of a parameter value, wherein the controller is configured to change the mask pose based on the parameter value;

saving, by the system, the desired parameter value;

finding, by the system, an actual value of the parameter;

querying, by the system, whether the actual parameter value agrees with the desired parameter value;

determining, by the system, that the actual parameter value does not agree with the desired parameter value;

adjusting, by the system, a system setting so as to attain the desired parameter value;

querying, by the system, whether the actual revised parameter value agrees with the desired parameter value; and repeating, by the system, the steps of determining, adjusting, and querying whether the actual revised parameter value agrees with the desired parameter value until the actual revised parameter value agrees with the desired parameter value.

* * * * *